(12) United States Patent
Grafinger

(10) Patent No.: US 7,597,716 B2
(45) Date of Patent: Oct. 6, 2009

(54) KNEE JOINT PROSTHESIS

(76) Inventor: Josef Grafinger, Ottakringerstrasse 215/4/5/7, A-1160 Vienna (AT)

( * ) Notice: Subject to any disclaimer, the term of this patent is extended or adjusted under 35 U.S.C. 154(b) by 0 days.

(21) Appl. No.: 11/658,378

(22) PCT Filed: Dec. 2, 2004

(86) PCT No.: PCT/AT2004/000421
§ 371 (c)(1),
(2), (4) Date: Aug. 28, 2008

(87) PCT Pub. No.: WO2006/007605
PCT Pub. Date: Jan. 26, 2006

(65) Prior Publication Data
US 2009/0043401 A1    Feb. 12, 2009

(30) Foreign Application Priority Data
Jul. 23, 2004    (AT) ............................... A 1259/2004

(51) Int. Cl.
*A61F 2/62* (2006.01)

(52) U.S. Cl. ...................................................... 623/39
(58) Field of Classification Search ............... 623/39–46
See application file for complete search history.

(56) References Cited

U.S. PATENT DOCUMENTS 1,390,915 A * 9/1921 Loth ............................ 623/39

* cited by examiner

*Primary Examiner*—Bruce E Snow
(74) *Attorney, Agent, or Firm*—Andrew Wilford

(57) ABSTRACT

The invention relates to a knee joint prosthesis comprising two arched guiding elements (3, 4) with a variable curvature in a first body (1) associated with the thigh, bolts (6, 7), or the like, of a second body (2) associated with the lower leg engaging in said guiding elements. The points $X_P(\phi), Y_P(\phi)$ of one guiding element (3) and the points $X_Q(\phi)$ and $Y_Q(\phi)$ of the other guiding element (4) correspond approximately to the following equations: $X_P(\phi)=A1\times\phi^5+B1\times\phi^4+C1\times\phi^3+D1\times\phi^2+E1\times\phi-F1$; $Y_P(\phi)=A2\times\phi^5+B2\times\phi^4+C2\times\phi^3+D2\times\phi^2+E2\times\phi-F2$; $X_Q(\phi)=A3\times\phi^5+B3\times\phi^4+C3\times\phi^3+D3\times\phi^2+E3\times\phi-F3$; $Y_Q(\phi)=A4\times\phi^5+B4\times\phi^4+C4\times\phi^3+D4\times\phi^2+E4\times\phi-F3$, the deflection angle f of the knee joint being indicated in radians. The inventive knee joint prosthesis enables a significant adaptation to the natural movement.

4 Claims, 3 Drawing Sheets

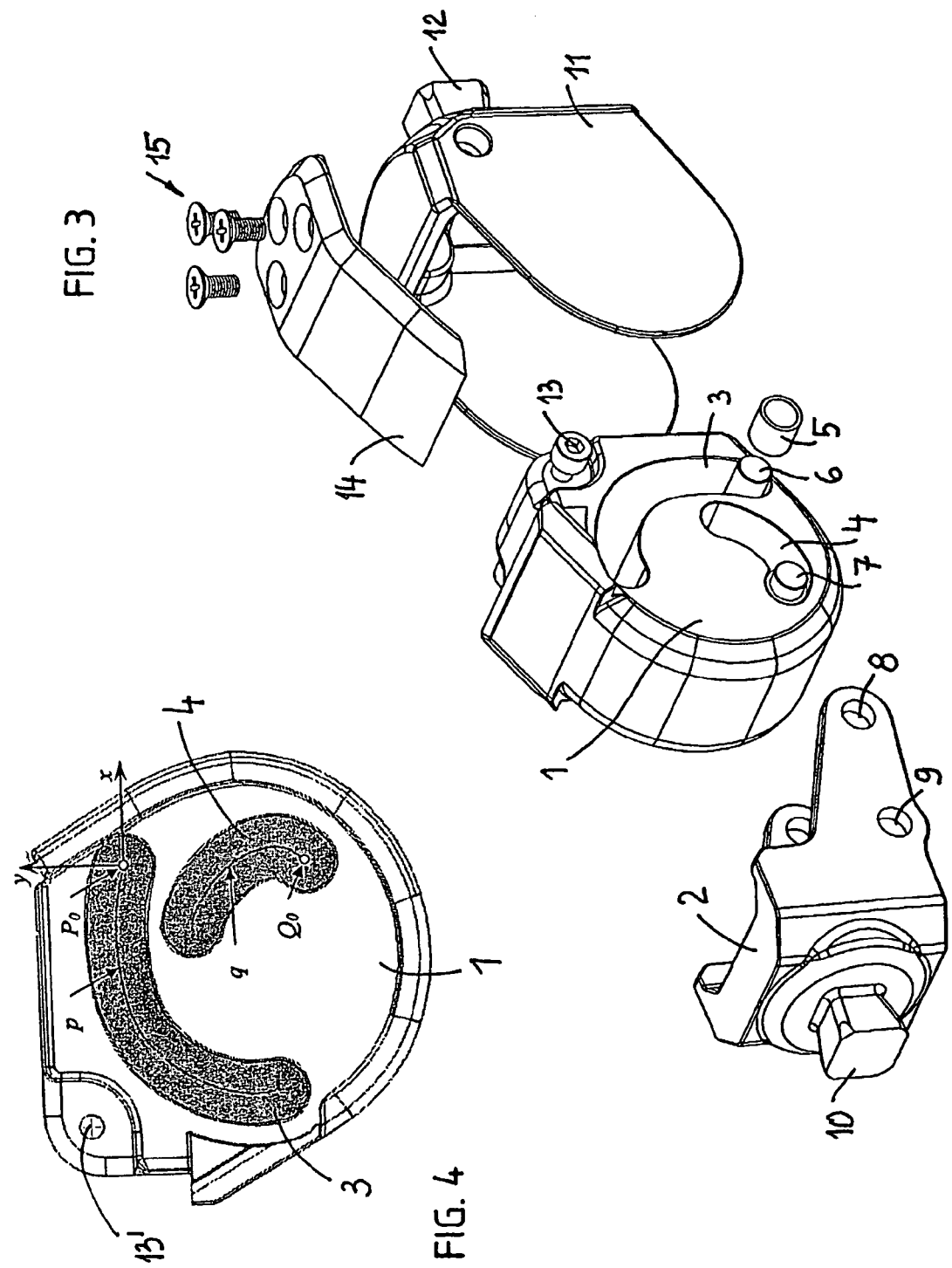

KNEE JOINT PROSTHESIS

CROSS REFERENCE TO RELATED APPLICATIONS

Figure 1:
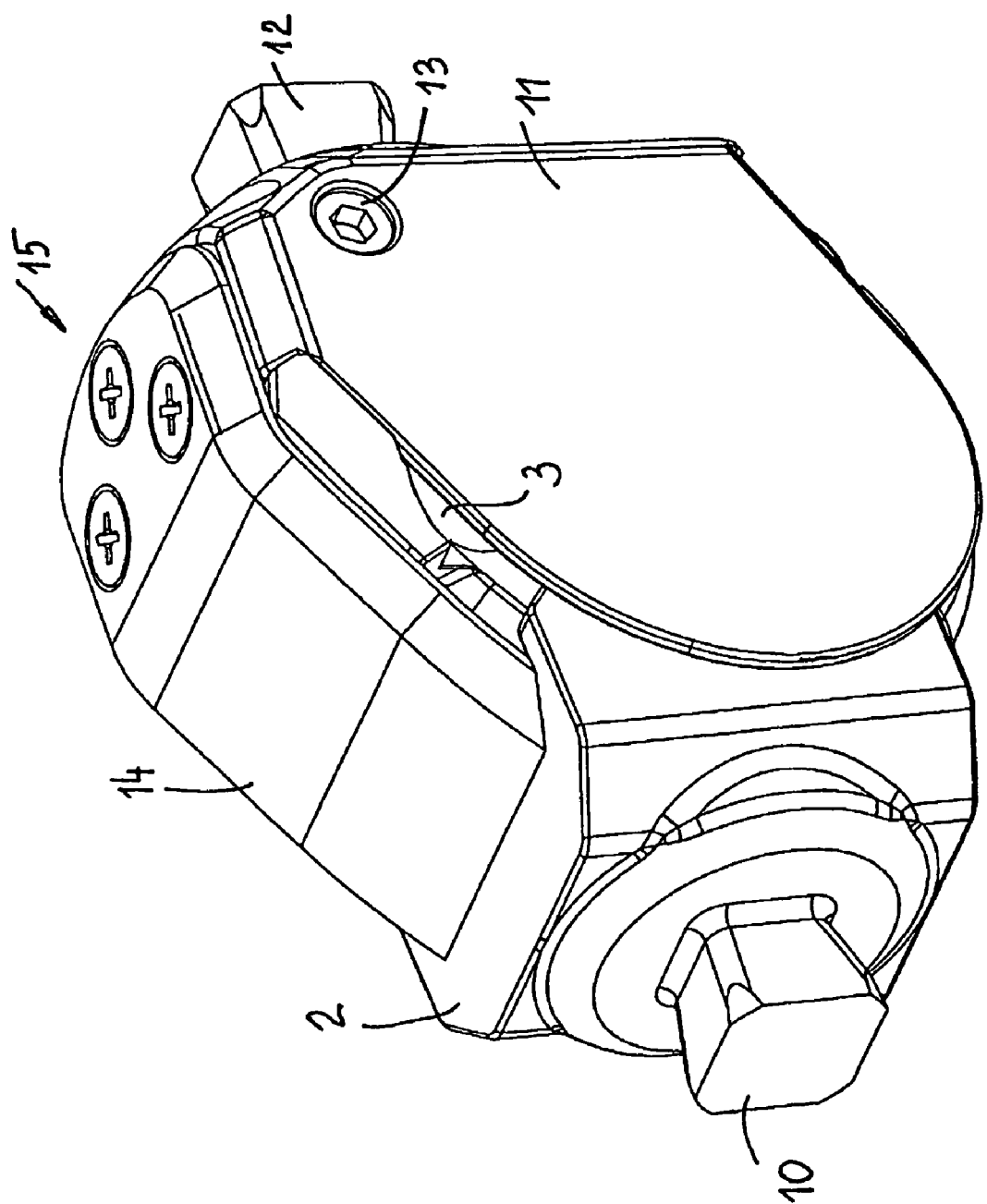

This application is the US national phase of PCT application PCT/AT2004/00421, filed 2 Dec. 2004, published 26 Jan. 2006 as WO 2006/007605, and claiming the priority of Austrian patent application A12592004 itself filed 23 Jul. 2004.

The knee joint is of particular importance in the provision of prostheses for transfemural amputations. As well as providing mechanical strength and load support, it must also meet specific functional requirements. On the one hand, when standing still and in the phase of the leg being the standing leg when walking, it must not bend. On the other, the dynamic behaviour during the late phase as the standing leg and in the swinging leg phase must be such as to allow for the most natural gait possible despite the missing musculature. Different systems may be used, depending on the agility of the patient being provided for. If, for example with fragile patients, the stability argument is the prime consideration, then with younger and more active patients the attempt should be made to meet their desires for movement as far as possible. There is accordingly a wide range of products on the market, starting from the simple hinged joint through to multi-axis joints (poly-centric joints). These joints, however, can also be equipped with additional mechanical and electromechanical components, such as mechanical locks, return springs, hydraulic dampers, or even computer-controlled damping elements.

As research has shown, the momentary centre of rotation of the natural human knee joint changes location, as a rule towards the rear (dorsal) as the flexure increases in relation to the femur. Accordingly, when providing orthopaedic assistance, the attempt should be made to imitate this behaviour, which is explained by the kinematics of the joint square formed by the cruciate ligaments during the rolling motion.

In AT 393 620 B, this joint square is imitated by two circular guiding elements. The kinematics of the human knee joint are, however, far more complex, and the idealised view of the crucial ligaments as rigid rods of a joint square is only an approximation of the true behaviour.

By contrast with this, the effort is made with prosthetic joints to achieve the migration of the centre of rotation from the rear to the front, in order to guarantee sufficient security against folding in the standing leg phase.

The object of the invention is to create a prosthetic knee joint which is as simple as possible in design and accords with all the essential requirements of the user.

This is achieved in that two arched guiding elements of variable curvature are provided in a first body associated with the thigh, engaging into which are bolts or the like of a second body associated with the lower leg, and the points $X_P(\phi)$, $Y_P(\phi)$. of the one guiding element, and the points $X_Q(\phi)$ and $Y_Q(\phi)$ of the other guiding element correspond approximately to the following equations:

$$X_P(\phi) = A1 \times \phi^5 + B1 \times \phi^4 + C1 \times \phi^3 + D1 \times \phi^2 + E1 \times \phi - F1$$

$$Y_P(\phi) = A2 \times \phi^5 + B2 \times \phi^4 + C2 \times \phi^3 + D2 \times \phi^2 + E2 \times \phi - F2$$

$$X_Q(\phi) = A3 \times \phi^5 + B3 \times \phi^4 + C3 \times \phi^3 + D3 \times \phi^2 + E3 \times \phi - F3$$

$$Y_Q(\phi) = A4 \times \phi^5 + B4 \times \phi^4 + C4 \times \phi^3 + D4 \times \phi^2 + E4 \times \phi - F4$$

whereby the deflection angle $\phi$ of the knee joint is indicated in radians.

The coefficients can in this situation assume negative values.

With a knee joint prosthesis according to the invention, the migration of the momentary centre of rotation is the prime requirement. The guiding elements are designed in such a way that they do not describe circular trajectories. Accordingly, no roll-over joint square is formed.

The coefficients of the equations given above can be adapted to meet individual requirements. With one knee joint prosthesis tested in experiments, the points $X_P(\phi)$, $Y_P(\phi)$ of the one guiding element and the points $X_Q(\phi)$ and $Y_Q(\phi)$ of the other guiding element correspond approximately to the following equations:

$$X_P(\phi) = 2.5468\phi^5 - 13.3577\phi^4 + 27.2734\phi^3 - 25.0789\phi^2 - 14.3902\phi - 0.0195$$

$$Y_P(\phi) = -2.0355\phi^5 + 8.4168\phi^4 - 11.4013\phi^3 + 0.3239\phi^2 + 5.5098\phi + 0.0201$$

$$X_Q(\phi) = 2.6774\phi^5 - 12.9957\phi^4 + 21.7884\phi^3 - 24.8599\phi^2 + 15.9312\phi - 0.0179$$

$$Y_Q(\phi) = -1.8306\phi^5 + 6.7402\phi^4 - 10.9995\phi^3 + 15.3202\phi^2 + 5.5433\phi - 30.3853$$

With a purposeful embodiment of the invention which is particularly easy to manufacture, the first body is engaged around in fork fashion by the guiding elements of the second body, with the mountings of the bolts and with a connection for the lower leg.

It is further to advantage if the second body with the mountings of the bolts or the like, and the connection for the lower leg are engaged around in fork fashion by a cover with a connection for the lower leg, whereby the cover is connected to the first body in a detachable manner.

With such an embodiment, the knee joint prosthesis can be easily dismantled into its individual components. As a result, the possibility is achieved for an individual and yet simple arrangement of the kinematics of the knee joint prosthesis and for its adaptation to the requirements of the prosthetic provision for patients with transfemural amputation.

Within the framework of the invention, it is further to the purpose if the detachable connection consists of at least one screw running approximately parallel to the bolts or the like.

In addition, the cover can also be arranged on the plate lying on the first body.

The invention is explained in greater detail hereinafter on the basis of an embodiment represented in the drawings, without it being restricted to this example.

Figure 2:
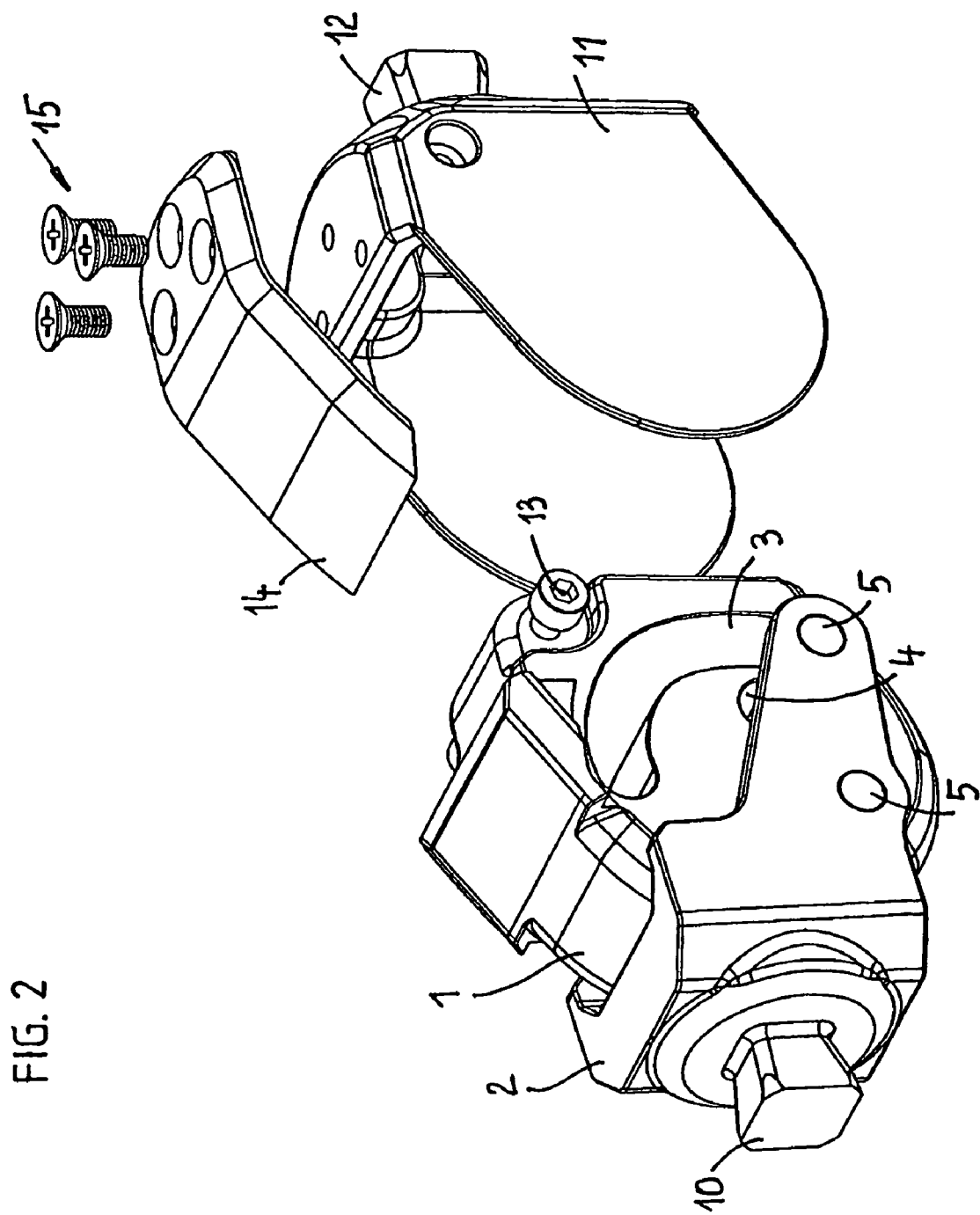

The drawings show:

FIG. 1 A diagrammatic view of a knee joint prosthesis according to the invention;

FIG. 2 An exploded view of the knee joint prosthesis according to the invention, with the cover withdrawn;

FIG. 3 Likewise, an exploded view of the knee joint prosthesis with the cover withdrawn and the second body drawn off;

FIG. 4 The first body in a diagrammatic section, with the co-ordinate system entered.

According to the drawings, especially FIGS. 1 to 3, the knee joint prosthesis according to the invention comprises a first body 1, which is associated with the thigh, and a second body 2 associated with the lower leg. Arranged in the first body 1 are two arched guiding elements 3 and 4, the path of which is explained on the basis of FIG. 4.

Bolts 6 and 7 are guided in the guiding elements 3 and 4 by means of bearings 5, of which only one is shown. The bearings 5 of the bolt 6 are retained in apertures 8 of the body 2 and the bearings 5 of the bolt 7 in apertures 9 of the body 2. The bearings 5 with the apertures 8 and 9 therefore form the mountings of the bolts 6 and 7. The body 2 is provided with a connection 10, in the shape of a truncated pyramid, to the lower leg or its prosthesis.

In the assembled state, the body 2 engages around the body 1. Both bodies 1 and 2 are therefore necessarily guided in counter-directions.

The unit formed of the first and second bodies is engaged around in fork fashion by a cover 11, which is provided with a connection 12, in the shape of a truncated pyramid, to the thigh or its prosthesis. The cover 11 and the first body 1 are connected to one another by means of at least one screw 13. Arranged above this, in order to provide a detachable connection of the parts 1 and 11, is a plate 14, lying on the cover 11 and the first body 1. The plate 14 is connected to the cover 11 by means of screws 15.

FIG. 4 shows the path of the guiding elements 3 and 4. The hole 13' for the screw 13 in this situation is located in the front, in the position of use of the knee joint prosthesis as shown. The points $X_P(\phi)$, $Y_P(\phi)$, $X_Q(\phi)$, $Y_Q(\phi)$ determined in the characterisation sections of claim 1 and claim 2 respectively relate to the mid-lines p and q of the guiding elements 3 and 4. The origin of the co-ordinate system is relocated into the front end of the mid-line p.

Numerous variations are possible within the framework of the invention, and in particular the coefficients of the guiding elements can be adapted to suit individual requirements.

The invention claimed is:

1. A knee joint prosthesis with a first body associated with the thigh and a second body associated with the lower leg, which engages around the first body in fork fashion, whereby arched guiding elements with a variable curvature are provided in the first body, into which engage bolts of the like of the second body wherein in each of the limbs of the fork-shaped first body two guiding elements with a variable curvature are provided, whereby in each case a bolt or the like of the second body engages into each of the guiding elements, and the points $X_P(\phi)$, $Y_P(\phi)$ of the first guiding element and the points $X_Q(\phi)$, $Y_Q(\phi)$ of the other guiding element correspond approximately to the following equations:

$$X_P(\phi) = A1*\phi^5 + B1*\phi^4 + C1*\phi^3 + D1*\phi^2 + E1*\phi - F1$$

$$Y_P(\phi) = A1*\phi^5 + B1*\phi^4 + C1*\phi^3 + D1*\phi^2 + E1*\phi - F1$$

$$X_Q(\phi) = A1*\phi^5 + B1*\phi^4 + C1*\phi^3 + D1*\phi^2 + E1*\phi - F1$$

$$Y_Q(\phi) = A1*\phi^5 + B1*\phi^4 + C1*\phi^3 + D1*\phi^2 + E1*\phi - F1$$

whereby the deflection angle of the knee joint is indicated in radians, the points $X_P(\phi)$, $Y_P(\phi)$ of the first guiding element and the points $X_Q(\phi)$, $Y_Q(\phi)$ of the other guiding element corresponding approximately to the following equations:

$$X_P(\phi) = 2.5468\phi^5 - 13.3577\phi^4 + 27.2734\phi^3 - 25.0789\phi^2 - 14.3902\phi - 0.0195$$

$$Y_P(\phi) = -2.0355\phi^5 + 8.4168\phi^4 - 11.4013\phi^3 + 0.3239\phi^2 + 5.5098\phi + 0.0201$$

$$X_Q(\phi) = 2.6774\phi^5 - 12.9957\phi^4 + 21.7884\phi^3 - 24.8599\phi^2 + 15.9312\phi - 0.0179$$

$$Y_Q(\phi) = -1.8306\phi^5 + 6.7402\phi^4 - 10.9995\phi^3 + 15.3202\phi^2 + 5.5433\phi - 30.3853$$

where the deflection angle $\phi$ of the knee joint is indicated in radians.

2. The knee joint prosthesis according to claim 1 wherein the second body is engaged around in fork fashion by the mountings of the bolts, and the connection for the lower leg is engaged around in fork fashion by a cover with a connection for the thigh, whereby the cover is connected to the first body in a detachable manner.

3. The knee joint prosthesis according to claim 2 wherein the detachable connection consists of at least one screw running approximately parallel to the bolts.

4. The knee joint prosthesis according to claim 3 wherein a plate is arranged lying on the cover and on the first body.

\* \* \* \* \*